(12) United States Patent
Smith et al.

(10) Patent No.: US 12,298,247 B2
(45) Date of Patent: May 13, 2025

(54) RESONANCE RAMAN SPECTROSCOPY FOR EVALUATING MITOCHONDRIAL FUNCTION

(71) Applicants: Children's Medical Center Corporation, Boston, MA (US); Pendar Technologies, LLC, Cambridge, MA (US)

(72) Inventors: Lois Smith, West Newton, MA (US); Bertan D. Cakir, Brookline, MA (US); John Padraic Romfh, Cambridge, MA (US); Peili Chen, Cambridge, MA (US); Daryoosh Vakhshoori, Cambridge, MA (US)

(73) Assignees: Children's Medical Center Corporation, Boston, MA (US); Pendar Technologies, LLC, Cambridge, MA (US)

( * ) Notice: Subject to any disclaimer, the term of this patent is extended or adjusted under 35 U.S.C. 154(b) by 189 days.

(21) Appl. No.: 17/772,085

(22) PCT Filed: Oct. 27, 2020

(86) PCT No.: PCT/US2020/057563
§ 371 (c)(1),
(2) Date: Apr. 26, 2022

(87) PCT Pub. No.: WO2021/086869
PCT Pub. Date: May 6, 2021

(65) Prior Publication Data
US 2022/0373466 A1   Nov. 24, 2022

(51) Int. Cl.
*G01N 21/65*   (2006.01)
*A61B 3/10*    (2006.01)
(Continued)

(52) U.S. Cl.
CPC .............. *G01N 21/65* (2013.01); *A61B 3/102* (2013.01); *A61B 3/12* (2013.01); *G01J 3/44* (2013.01)

(58) Field of Classification Search
CPC ... A61B 3/10; A61B 3/102; A61B 3/12; G01J 3/44; G01N 21/65
See application file for complete search history.

(56) References Cited

U.S. PATENT DOCUMENTS 5,733,739 A    3/1998   Zakim et al.
5,842,995 A    12/1998  Mahadevan-Jansen et al.
(Continued)

FOREIGN PATENT DOCUMENTS

WO   WO 2008/029162 A1   3/2008
WO   WO 2019/126314 A1   6/2019

OTHER PUBLICATIONS

Invitation to Pay Additional Fees for International Application No. PCT/US2020/057563, mailed Dec. 9, 2020.
(Continued)

*Primary Examiner* — Hina F Ayub
(74) *Attorney, Agent, or Firm* — Wolf, Greenfield & Sacks, P.C.

(57) ABSTRACT

Apparatuses and methods for using Raman Resonance Spectroscopy to evaluate metabolic and oxygenation status of the eye are disclosed herein. In some embodiments, metabolic mapping of the eye may be performed by aligning a Raman spectrum and a recorded spatial image of the eye.

11 Claims, 15 Drawing Sheets

(51) Int. Cl.
*A61B 3/12* (2006.01)
*G01J 3/44* (2006.01)

(56) References Cited

U.S. PATENT DOCUMENTS

| | | |
|---|---|---|
| 5,873,831 A | 2/1999 | Bernstein et al. |
| 6,370,422 B1 | 4/2002 | Richards-Kortum et al. |
| 6,507,747 B1 | 1/2003 | Gowda et al. |
| 2001/0012429 A1 | 8/2001 | Wach et al. |
| 2003/0130579 A1 | 7/2003 | McClane et al. |
| 2006/0134004 A1 | 6/2006 | Gellermann et al. |
| 2008/0076985 A1 | 3/2008 | Matousek et al. |
| 2009/0021724 A1 | 1/2009 | Mahadevan-Jansen et al. |
| 2010/0105098 A1 | 4/2010 | Frederiske et al. |
| 2010/0241450 A1 | 9/2010 | Gierhart et al. |
| 2011/0244604 A1 | 10/2011 | Narazaki et al. |
| 2013/0172700 A1 | 7/2013 | Lan et al. |
| 2014/0085603 A1 | 3/2014 | Su et al. |
| 2015/0015879 A1* | 1/2015 | Papadopoulos ......... G02F 1/011 356/301 |

OTHER PUBLICATIONS

International Search Report and Written Opinion for International Application No. PCT/US2020/057563, mailed Feb. 16, 2021.

International Preliminary Report on Patentability for International Application No. PCT/US2020/057563, mailed May 12, 2022.

Erckens et al., Raman spectroscopy in ophthalmology: from experimental tool to applications in vivo. Lasers in Medical Science. Oct. 2001;16(4):236-52.

Erjavec et al., Raman spectroscopy as a tool for detecting mitochondrial fitness. Journal of Raman Spectroscopy. Aug. 2016;47(8):933-9.

Matthäus. Label-free detection of mitochondrial distribution in cells by nonresonant Raman microspectroscopy. Biophysical journal. Jul. 15, 2007;93(2):668-73.

Perry et al., Responsive monitoring of mitochondrial redox states in heart muscle predicts impending cardiac arrest. Science translational medicine. Sep. 20, 2017;9(408):eaan0117.

* cited by examiner

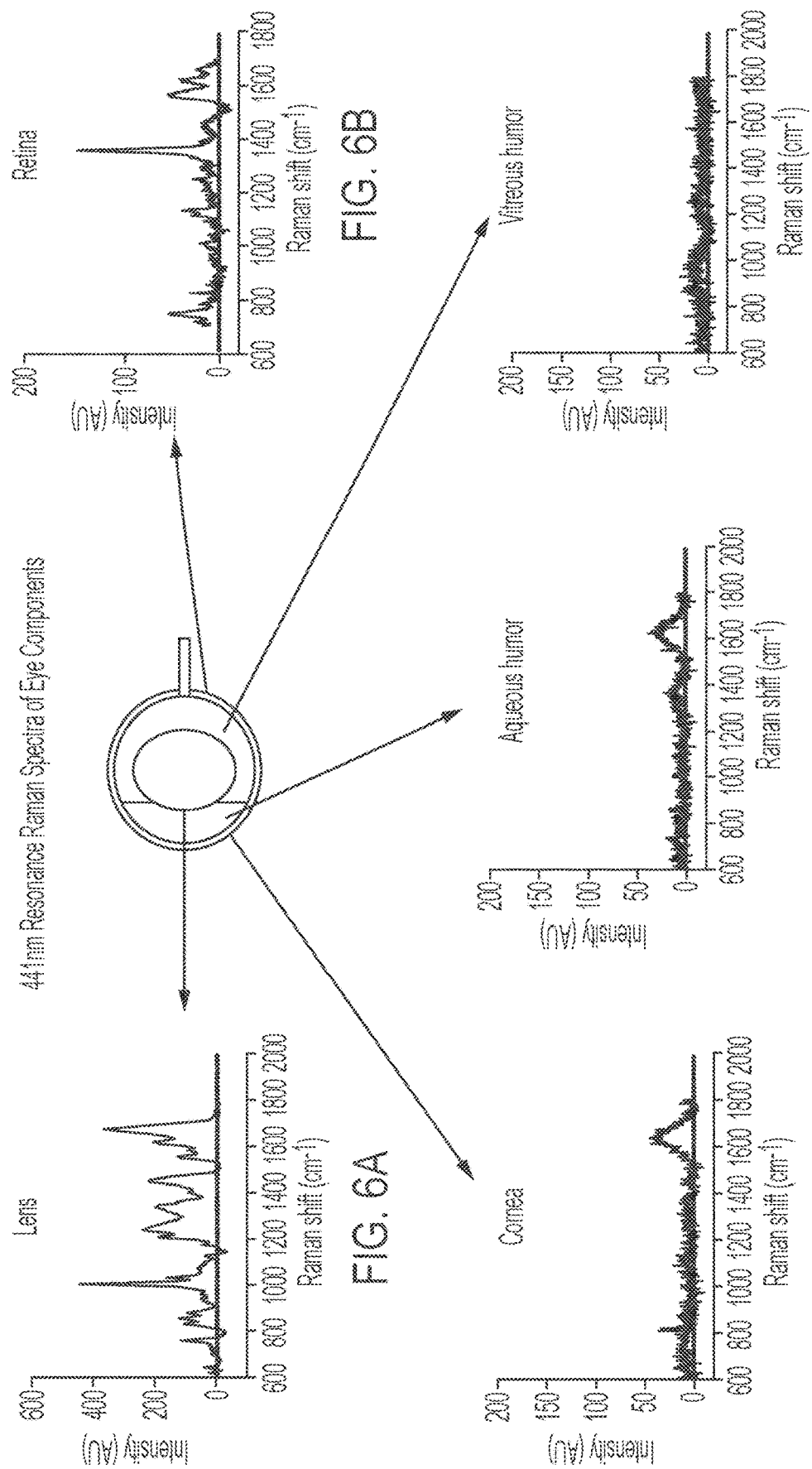

RESONANCE RAMAN SPECTROSCOPY FOR EVALUATING MITOCHONDRIAL FUNCTION

RELATED APPLICATIONS

This application is a national stage filing under 35 U.S.C. § 371 of international PCT application PCT/US2020/057563, filed Oct. 27, 2020, which claims the benefit under 35 U.S.C. § 119 (e) to U.S. Provisional Application No. 62/957,104, filed Jan. 3, 2020, and U.S. Provisional Application No. 62/926,940, filed Oct. 28, 2019, the contents of each of which are incorporated herein in their entireties.

FIELD

Devices and methods for using Resonance Raman spectroscopy in ophthalmology are disclosed herein.

BACKGROUND

Resonance Raman spectroscopy (RRS) is a non-contact, non-invasive, light-based method of providing information about the vibrational mode of a molecule. The retina is a highly metabolic tissue of the eye that converts light into electrical impulses, which are delivered to the brain via the optic nerve.

SUMMARY

According to one embodiment, a device includes a Raman spectrometer arranged to collect inelastic light, a Raman probe in communication with the Raman spectrometer, the Raman probe arranged to transmit light to a portion of a subject and collect the inelastic light back to the spectrometer, a first imager arranged to capture a spatial image of the portion of the subject.

According to another embodiment, a method of metabolically mapping an eye of a subject is disclosed. The method includes directing an incident light having a first wavelength on a retina of an eye of the subject, collecting inelastic scattered light from retinal tissue, filtering out one or more Raman signals, preparing a Raman spectrum, and calculating oxidized and reduced ratios and a total quantity of a first molecule.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 6A-6E illustrates a spectral library of components of an eye of a subject, with FIG. 6A being a Raman spectrum of the lens, FIG. 6B being a Raman spectrum of the retina, FIG. 6C being a Raman spectrum of the cornea, FIG. 6D being a Raman spectrum of the aqueous humor, and FIG. 6E being a Raman spectrum of the vitreous humor;

DETAILED DESCRIPTION

Figure 1:
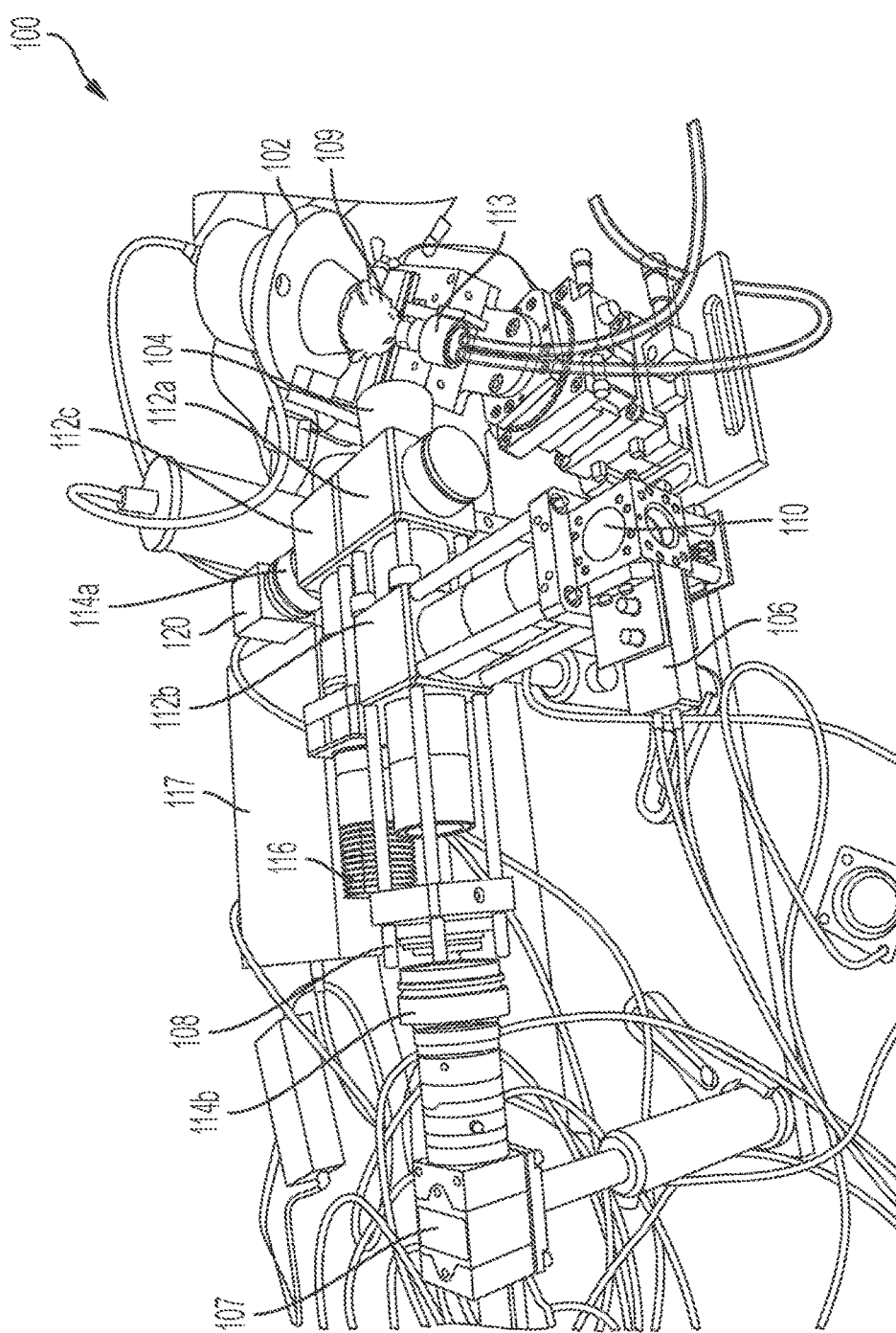
FIG. 1 is a testing device according to embodiments of the present disclosure.

Resonance Raman spectroscopy ("RRS") is a non-contact, non-invasive, light-based method of providing information about the vibrational mode of a molecule. Without wishing to be bound by theory, RRS uses light of a single emission spectrum to alter the vibrational mode of a molecule, which leads to a shift of the light by the amount absorbed (e.g., inelastic scattering or Raman shift). Because vibrational frequencies are unique to individual molecules, RRS may be used to identify the molecules present in a sample. For example, a sample may be illuminated via incident light at a specific wavelength, with a portion of the light being absorbed and the remainder being emitted as inelastic scatter that is unique to each molecule and is detectable. The intensity of the inelastic scattering may be quantified, and a Raman spectrum of that sample may be graphically displayed with a wavenumber (1/cm) on the x-axis and the intensity of the inelastic scatter on the y-axis (see, e.g., FIGS. 7A-7B). In some embodiments, RRS allows for precise identification of molecules in a complex environment.

RRS has been used in ophthalmology, such as to determine a level of macular pigments in the eye. In some embodiments, such a determination may be made because the frequencies on a Raman spectra associated with such pigments have already been established. In some embodiments, the presence or risk of a disease related to the macular tissue in the eye may been assessed based on a detected pigment level.

The inventors have recognized that advantages may be realized by using RRS to assess the metabolic and oxygenation status of the eye, such as the metabolic and oxygenation status of retina. As is known, the retina is a highly metabolically active tissue that converts light to electrical impulses, that are thereafter transmitted to the brain via the optic nerve. Without wishing to be bound by theory, mitochondrial function may depend on the current function, metabolism, or health of the cell, which can change quickly and at different conditions. In some embodiments, a decrease in mitochondrial function is associated with several diseases states of the eye, such as age related macular degeneration, diabetic retinopathy, Retinopathy of Prematurity ("ROP"), and glaucoma. Applicant has recognized that markers identifiable by RRS and indicative of mitochondrial function were not previously known.

The inventors have also recognized that in vivo evaluation of mitochondrial function, such as an evaluation of a mitochondrial redox state in the retina, choroid, and/or optic nerve, may help to define disease processes and stages for more specific and refined intervention. Without wishing to be bound by theory, the proton gradient necessary for mitochondrial ATP production is generated by passing electrons from an electron donor, such as NADH, from higher to lower energy levels. The ratio between reduced and oxidized forms may provide information about oxygen and energy supply to the tissue. In some embodiments, a high reduced ratio may be explained by the lack of a final electron acceptor oxygen and a high oxidized ratio may be explained by the lack of electron donors due to fuel shortage (e.g., low energy status). Such information may provide direct information about the metabolic state of the cell. The inventors have recognized that such a determination may be performed using RRS of the eye.

The inventors have also recognized that detecting proteins in the electron transport chain (complex I-IV) and proteins involved in oxygen transportation (e.g., hemoglobin and neuroglobin) may be used to determine the metabolic oxygenation status of the retina. Without wishing to be bound by theory, neuroglobin has been discussed as being an intermediary protein of the oxygen transport from hemoglobin in the bloodstream to the mitochondria in cell. Traditionally, only detection of oxygen hemoglobin saturation in big vessels is currently achievable non-invasively. The inventors have recognized that oxygen hemoglobin saturation is detectable in the capillary bed via RRS.

In embodiments disclosed herein, the inventors have performed RRS on the retina of mice and gathered Raman spectra when the oxygenation of the eye, such as the oxygenation of the retina, is at different known levels. In this regard, the inventors have discovered a correlation between the oxygenation levels of the retina and frequencies identifiable on a Raman spectra. With such a correlation, during future testing, a Raman spectra may be used to determine the corresponding oxygenation of the retina by identifying the reduced and oxidized ratio of mitochondrial complexes. For example, the total quantity of each molecule and the oxidized and reduce ratio of those molecules may be quantified using RRS. The inventors have recognized that reduced and oxidized ratio of these proteins may enable the detection of dynamic changes in oxygen and energy metabolism.

The inventors have also recognized that that the oxygenation status and/or mitochondrial function of the retina may be indicative of disease progression. For example, the oxygenation level may be reduced at certain stages of a disease as compared to other stages of the disease. Thus, by performing RRS on the retina and using the Raman spectra to determine the corresponding oxygenation status, the mitochondrial function and disease state can be established. Such testing can be performed repeatedly (e.g., hourly, daily, weekly, monthly, or even yearly), with the change in oxygenation levels and change in disease state being documented. As will be appreciated, although oxygenation status has been described as being a marker for different states of a disease, other biomarkers in the retina also may be indicative of disease progression.

In some embodiments, as will be described, the inventors have simulated different stages of glaucoma in mice and measured corresponding Raman spectra. In such embodiments, the inventors hypothesized that by correlating the Raman spectra with known identifiable disease states (e.g., different stages of cell death), a later disease state may be identified sooner, which may prevent more serious and permanent injuries (e.g., blindness) from occurring.

The inventors have also recognized that RRS can be combined with other techniques, such as fundus photography, Optical Coherence Tomography ("OCT"), or another suitable imaging technique, to metabolically map the retina and align the metabolic mapping with morphological changes. For example, at the same time or in sequence with RRS, a spatial mapping of the eye, such as via OCT, may be performed, and this spatial mapping may be aligned with the RRS spectrum. As will be appreciated, by aligning the morphology with the RRS spectra, an additional correlation between visible indicia of a disease state and the Raman spectra is obtainable. For example, as will be described, Raman light may be directed towards a portion of the eye (e.g., the retina), with the light being superimposed over an image of the eye (e.g., an image captured via OCT or fundus photography). In some embodiments, by matching the Raman light with the OCT image or fundus image, the disease state of an identified portion of the eye may be determined.

The inventors have further recognized that RRS may be used to monitor brain function and other systemic disorders, such as ones in critically ill patients. For example, since the retina is part of the central nervous system, the retina reflects, in part, brain function. Thus, RRS of the retina may be performed to gather Raman spectra that may, in turn, provide information regarding brain function. As will be appreciated, RRS spectra may be used to determine oxygenation level of the retina, which may correlate to different metabolic states and brain function. In some embodiments, such a non-invasive technique may be used to monitor brain function of critically ill patients in the ICU.

Figure 2:
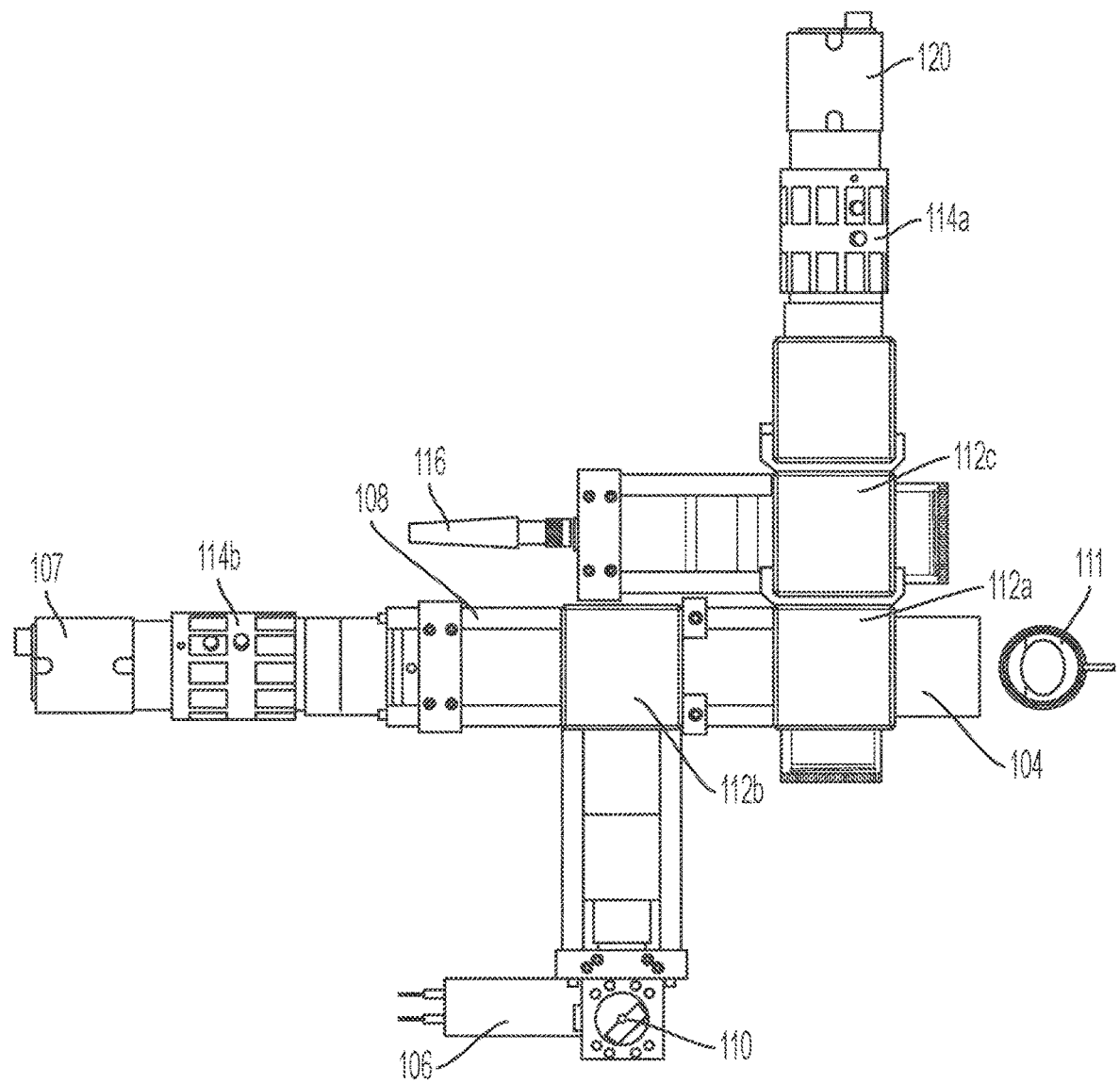
FIG. 2 is a schematic top view of a portion of the testing device of FIG. 1.
Figure 3:
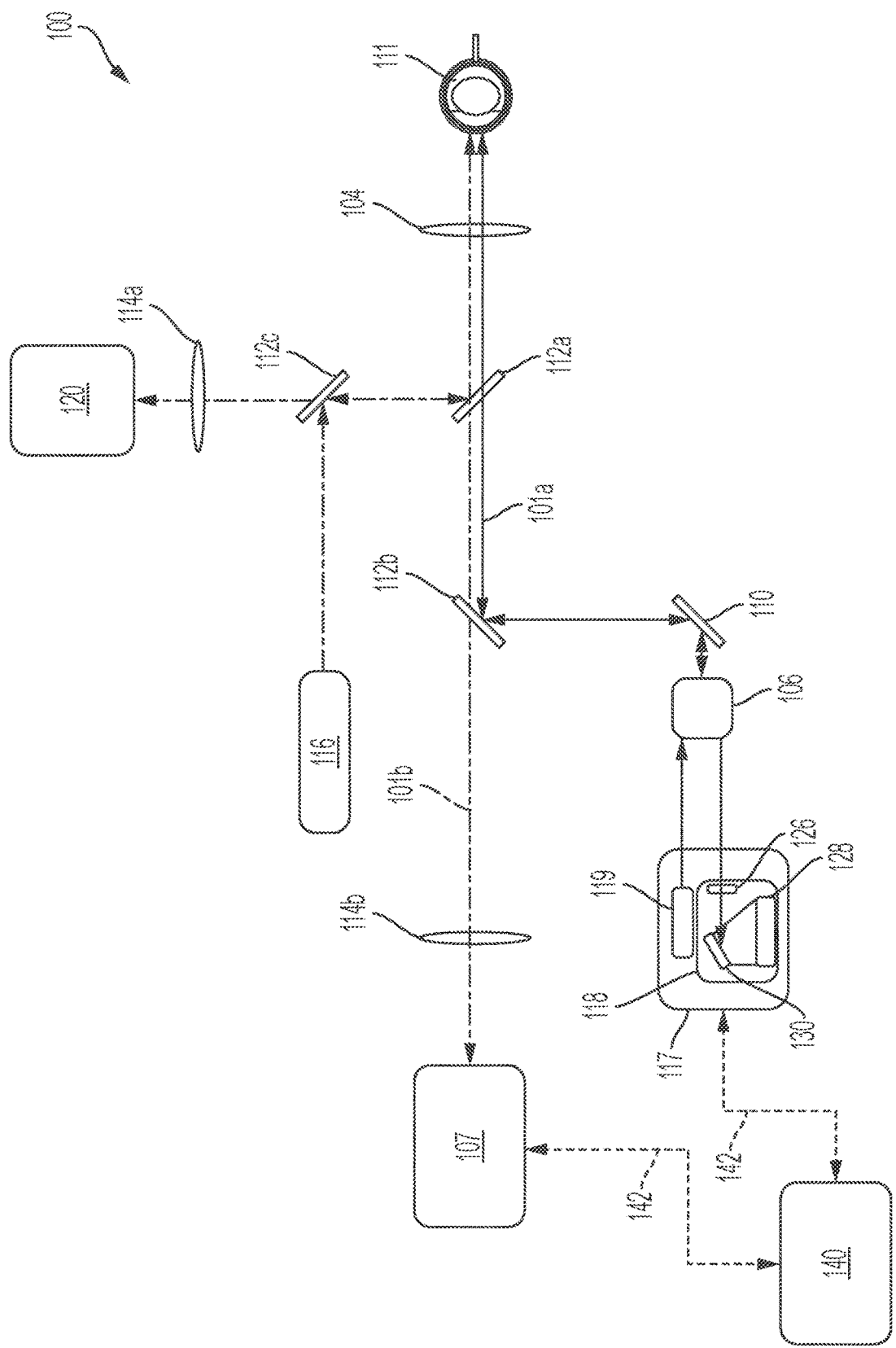
FIG. 3 is a schematic representation of a testing device according to some embodiments.

FIGS. 1-3 illustrates a testing device 100, also referred to herein as the device, according to embodiments of the present disclosure. As shown in these views, the testing device may be arranged to perform RRS on a subject (see the Raman path labeled 101a in FIG. 3), such as RRS on a retina of a rodent 109 (see FIG. 1). The testing device also may be arranged to capture an image of the subject (see the imaging path labeled 101b in FIG. 3). For example, the device may be arranged to image the retina of the rodent's eye 111 (see FIG. 2), via OCT or via a fundus camera. In some embodiments, as will be described, the device may be arranged to direct a Raman light on top of an OCT image or fundus image of the subject (see, e.g., FIG. 4). In some embodiments, the superimposed images may be visualized on an electronic device, such as on a monitor or on a mobile device (see, e.g., the user interface 200 in FIG. 5).

As shown in FIG. 1, the testing device 100 may include an adjustable holder 102, such as a stage or platform, arranged to hold the subject during testing. For example, the stage may adjust the position of the subject with respect to the testing device. In some embodiments, the stage may be moveable to align a portion of the subject, such as the eye of the subject, with the testing device. For example, the eye 111 (see FIG. 3) of the subject may be aligned with an objective lens 104 for testing. In some embodiments, the objective lens may be connected to a Raman probe 106 and/or a Fundus camera 107. In some examples, the stage may be used to adjust a laser spot on the retina of the rodent. In some embodiments, the objective lens is a 1-inch lens.

In some embodiments, the holder may be heated. In some embodiments, the holder may be rotated with 360 degrees of freedom. In some embodiments, such as that shown in FIG. 1, the holder may have a substantially circular cross-sectional shape, although the holder may have other shapes, such as square, oval, triangular, other polygonal, or other shapes. In some embodiments, the size of the opening of the holder may be adjustable. For example, the diameter of the holder may be increased or decreased depending upon the size of the rodent to be held. For example, the size of the opening may be increased for performing RRS on larger rodents and may be decreased for performing RRS on smaller rodents.

In some embodiments, as shown in FIG. 1, the apparatus may include a cone 113 which may be placed over the nose and/or mouth of the rodent. In some embodiments, the cone 113 is arranged to supply anesthetic (e.g., via inhalation) to the rodent. The cone 113 also may be arranged to supply and also to change the oxygen concentration supplied to the rodent. For example, the cone 113 may increase or decrease the level of oxygen supplied to the rodent to simulate conditions of normoxia and/or hypoxia.

In some embodiments, as shown in FIGS. 1 and 2, the device may include a frame 108 arranged to hold one or more testing components of the testing device. For example, the frame may be arranged to hold the Raman probe 106, the Fundus camera 107, one or more scanning mirrors 110, one or more beam splitters 112a-c, one or more focusing lenses 114-b, and/or an illumination source 116. The frame also may be arranged to hold an anterior segment camera 120. As will be appreciated, all of the testing components need not be attached to the frame. For example, as shown in FIG. 1, a housing 117 with a Raman spectrometer 118 (see FIG. 3), which includes a charge coupled device (CCD), and an excitation source 119, may be placed on a surface next to the frame holding the various testing components.

In some embodiments, the frame may include one or more sub frames to which the testing components are attachable. In some embodiments, the one or more sub frames may be rigidly attached to one another. The one or more sub frames also may be moveable relative to one another.

In some embodiments, the one or more testing components may be removably attachable to the frame. In such embodiments, a position of a first testing component in the device may be adjustable relative to a position of a second testing component in the testing device. In other embodiments, one or more testing components may be slidably attached to the frame such that the position of the first testing device may be adjustable relative to the position of the second testing device and/or to a position of the subject (or where the subject will be held in the testing device). For example, a component of the testing device may be moved longitudinally, laterally, or rotated relative to the frame and/or the subject (or to where the subject is held). In other embodiments, one or more testing components may be fixedly attached to the frame.

Figure 4:
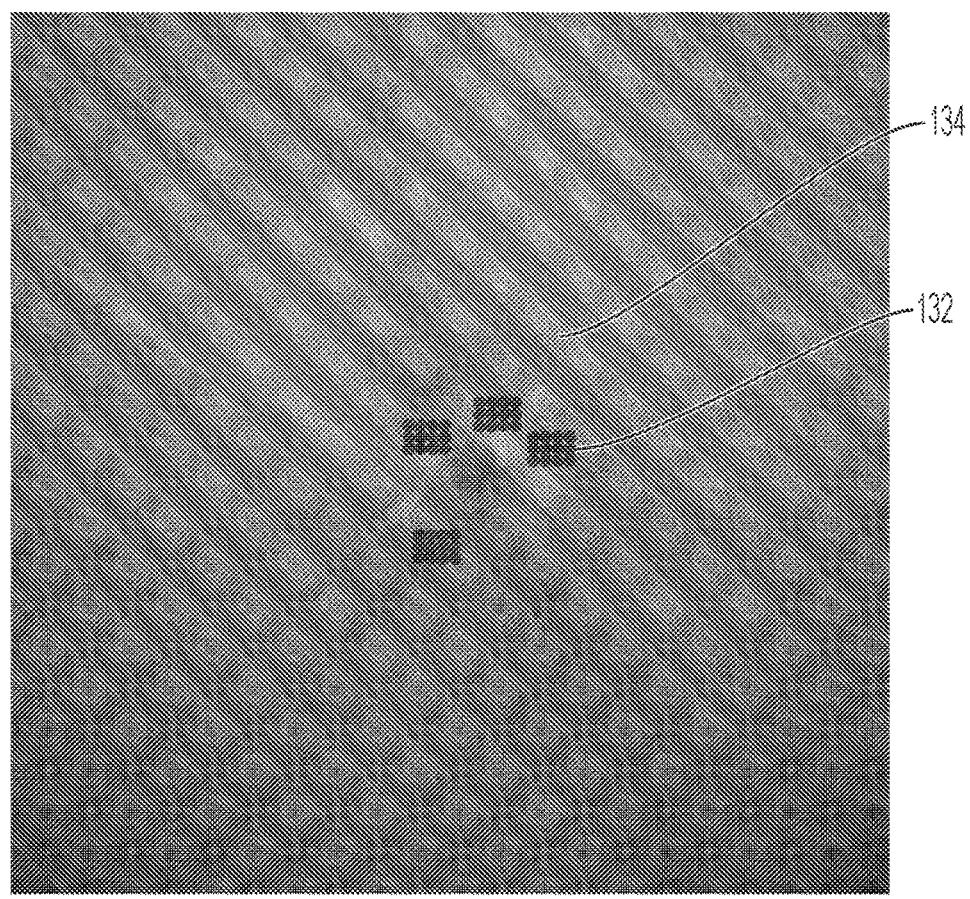
FIG. 4 is an image of a retina of an eye of a rodent taken with a testing device according to embodiments of the present disclosure, with Raman light directed at an optic nerve of the eye and superimposed over an image of the eye.
Figure 5:
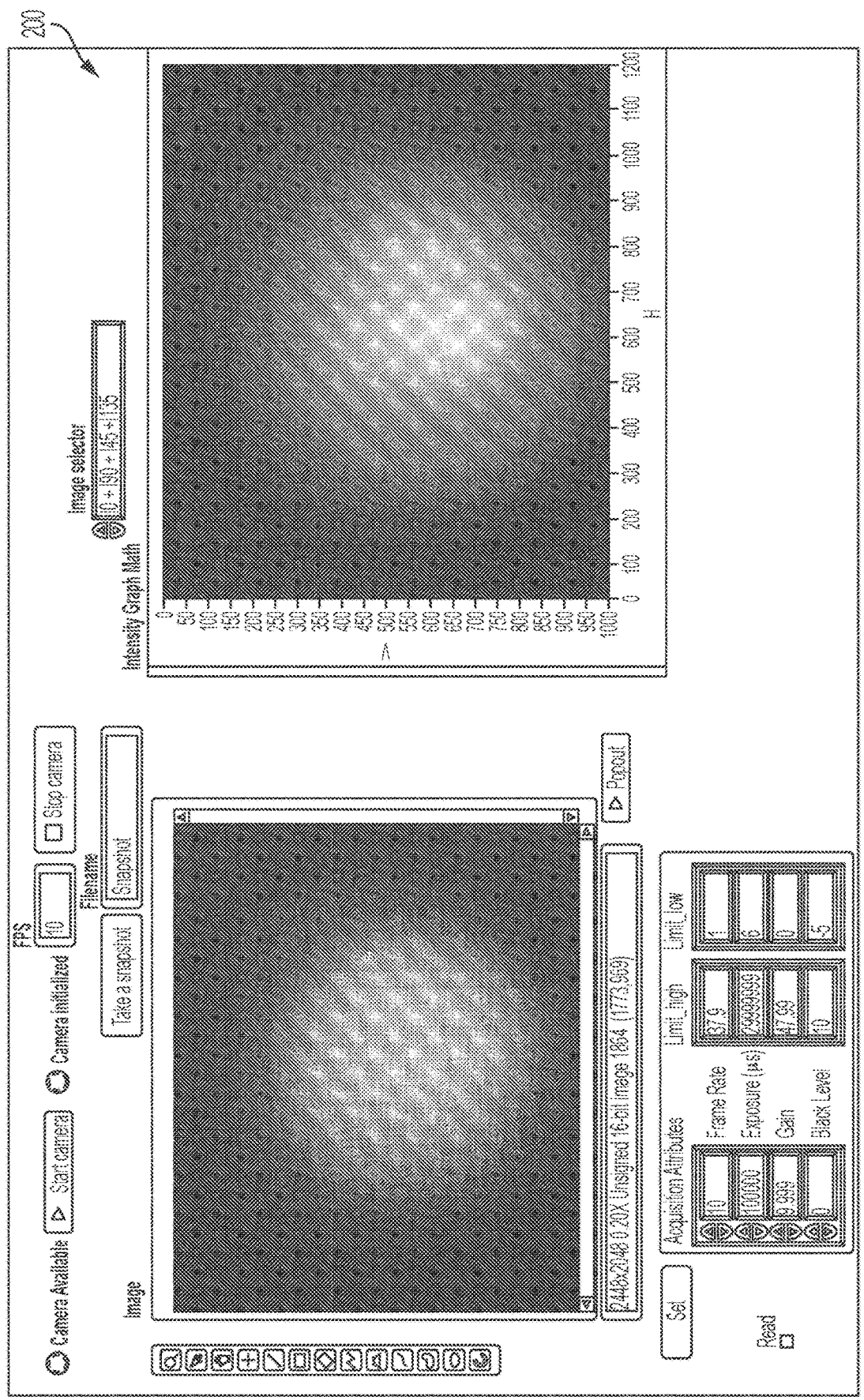
FIG. 5 is an example of a user interface of a testing system according to some embodiments.

As shown in FIG. 1-3, the device 100 may be arranged to perform RRS on the subject, such as on the eye of a rodent (see path 101a). In such embodiments, a light excitation source 119 may supply an excitation laser to the Raman probe 106, which transmits light to the eye 111 of the subject. As shown in FIG. 3, in some embodiments, the light is directed first to a scanning mirror 110 that may adjust the size and position of the light on the subject for scanning. For example, as shown in FIG. 4, in some embodiments, four scanning areas 132 may be directed towards the retina 134 of the eye of the subject.

In some embodiments, the scanning areas may be substantially rectangular in shape, although other suitable shapes may be used for testing (e.g., square, circle, triangle, other polygonal shape or other shape). In some embodiments, more or fewer scanning areas may be used for RRS testing. As will be appreciated, the position of the scanning areas relative to the retina (or other region being RRS tested) may be determined by visualizing of subject. For example, as shown in FIG. 4, the testing device may capture an image of the part of the subject being tested (e.g., the retina), with the scanning area(s) being shown superimposed over the image. In such an example, the scanning areas may be shown as blue light on the image of the retina. In some embodiments, visualization may be performed in real time, such that a technician may visualize the retina (or other region being RRS tested) and the relative size and position of the scanning area(s) while the scanning mirror is adjusting the light, such that the desired size and location of the scanning area(s) may be obtained.

In some embodiments, the wavelength of light is chosen such that it will elicit a Raman response in the retina being examined. As will be appreciated, the laser used in this apparatus may be configured to transmit light having a wavelength and power that are low enough to not damage the eye but yet high enough to stimulate the molecules and observe the vibrational frequencies and Raman shift. In some embodiments, the laser may be rastered to decrease toxicity (e.g., which could possibly damage the eye) and also decrease the signal to noise ration.

In some embodiments, the wavelength of the excitation laser may be optimized for each protein (oxidize and reduced) according to their absorption maximum. For example, the eye (e.g., the retina) may be excited with an incident light having a wavelength near the absorption maximum of a particular protein. In such an example, optimizing the wavelength for each molecule causes the signal strength and signal to noise ratio to be improved. For example, the spectral signature for each molecule may be orders of magnitude above the background when the wavelength has been optimized.

In some embodiments, the size of the laser may be selected to accommodate the size of the subject on which RRS is performed. For example, the laser may have a narrower diameter to accommodate a variety of smaller animal sizes (e.g., rodents). In some embodiments, the laser may be arranged to scan across the retina (e.g., for a raster scan). In other embodiments, the laser may be arranged to just scan the retina in a single position.

As shown in FIG. 3, in some embodiments, the light may pass from the scanning mirror 110 to a beam splitter 112b before reaching the eye 111 of the subject. As shown in FIG. 3, and as will be described, beamsplitters also may be used as part of the imaging path. In such embodiments, the testing device may include interchangeable beamsplitters that are arranged with filter properties for different conditions.

According to some embodiments, the Raman spectrometer may be arranged to both transmit the incident light and collect the inelastic light. In such embodiments, as shown in FIG. 3, the Raman spectrometer 118 may include a laser filter 126 for filtering the elastically scattered light. As will be appreciated in view of the above, the elastically scattered light results from the light from the Raman probe being directed onto the eye of the subject. In some embodiments, the Raman spectrometer also includes a charge coupled device (CCD) detector 128. The spectrometer may further include grating 130, which may be arranged to disperse signal onto the CCD by deflecting each wavelength of the scattered light at a different angle. In some embodiments, the CCD detector may assist with visualization of the retina. As described above, the quantity and intensity of the wavelengths may be graphically displayed on a Raman spectrum (see, e.g., FIGS. 6A-6E). In some embodiments, the testing device may include a computer system 140 that may store detected information and also create and display the graphical Raman spectra.

As will be appreciated, the device may have one-directional communication with the computer system 140. For example, each of the Raman spectrometer and Fundus camera may communicate with the computer system 140, such as to store the data from the testing. In other embodiments, the device may have bi-directional communication with the computer system. For example, the computer system may be arranged to send testing instructions to the testing device, and to also receive data for storing. As will be appreciated, the device may communicate with the computer system via any suitable manner (e.g., wired, wireless, Bluetooth).

In some embodiments, as shown in FIGS. 1-3, the device may be arranged to image a portion of the subject, such as the eye of the subject. For example, the device may be arranged to create an image of the eye (e.g., to see the structure of the eye). In some embodiments, imaging may be performed via the fundus camera 107. As will be appreciated, although the device is shown and described as having a fundus camera, an OCT camera may be used in other embodiments to image the portion of the subject.

As shown in FIG. 3, as part of the path 101b, an illumination source 116 may direct light toward the eye 111 of the subject. In some embodiments, the light may pass through beam splitters 112a, 112b before reaching the eye. As will be appreciated, although the light is shown as passing through two beam splitters in this view, it will be appreciated that device may have more or fewer beam splitters in other embodiments. As shown in FIG. 3, the light may be reflected off of the eye and travel back to the fundus camera 107. The light also may travel to an anterior segment camera 120 in some embodiments. As shown in FIGS. 1-3, both the fundus camera 107 and the anterior segment camera 120 may have a focusing lens 114b, 114a, which may be tunable such that the respective camera may obtain crisp images. For example, the lens may be adjustable to a certain range to obtain sharper images.

In some embodiments, the device may be used to create a metabolic map of the retina. For example, the device may capture an image of the structure of the retina, such as via the fundus camera, while also performing RRS testing of the retina. In such embodiments, the Raman spectra may be analyzed, to determine the amount of a particular molecule in the eye (e.g., in the retina). The recorded value may be correlated with a particular structure being visualized in the eye. For example, a particular disease state may be correlated with a measured value of a particular molecule in the eye.

Figures 7A, 7B:
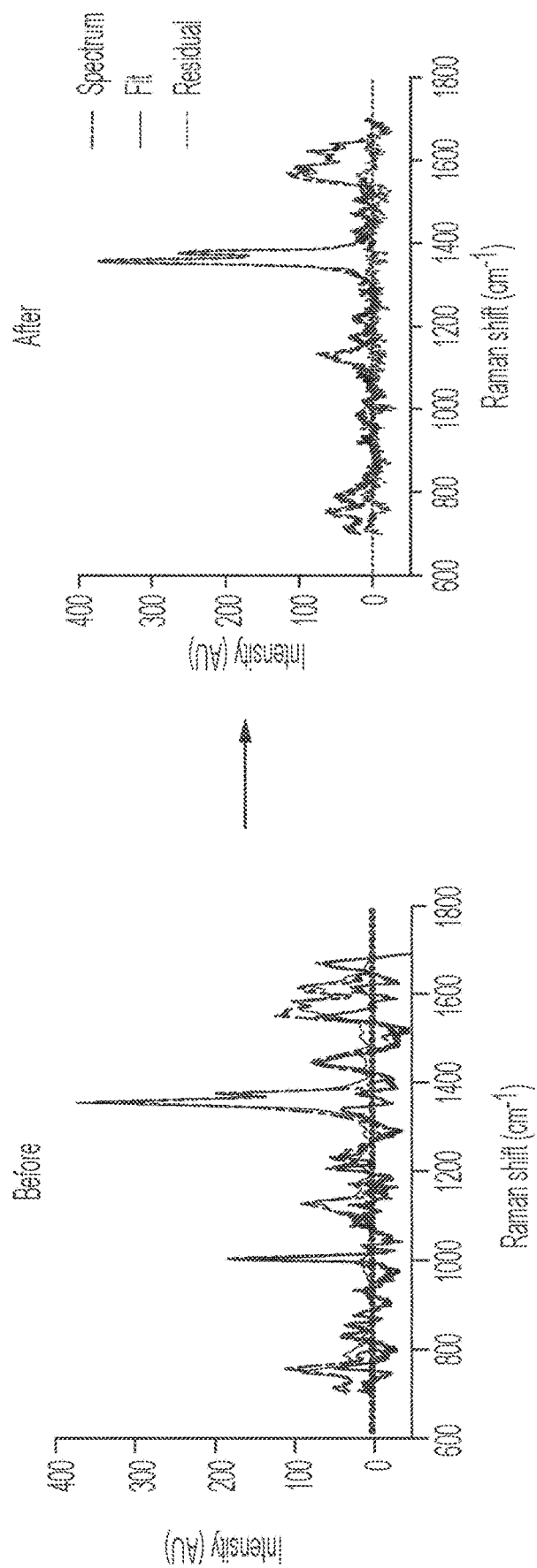
FIG. 7A is a Raman spectrum of an in vivo retina excited with a 441 nm incident light and FIG. 7B is a Raman spectrum after regression analysis with a spectral library.

As previously described, the retina may be excited with an incident light during RRS testing. In some embodiments, the excitation light may include a laser with a wavelength between 400 nm and 800 nm. For example, the retina may be excited with a 441 nm incident light in some embodiments. In some embodiments, prior to reaching the retina, the incident light may pass through the cornea, aqueous humor, lens, and/or vitreous humor of the eye. In such embodiments, unwanted Raman spectra may be created from the light passing through the other components of the eye. For example, as shown in FIG. 7A, the Raman spectra of an in vivo test of the eye may include frequencies corresponding to multiple components of the eye. Although the RRS is being described for testing of the retina, with unwanted scattered light coming from all other the noted components of the eye, in other embodiments, another component of the eye may be examined (e.g., the lens) with less unwanted Raman spectra being created. For example, when another component (e.g., the lens) of the eye is being tested, the light may pass through fewer other components, thus generating fewer unwanted Raman spectra.

FIGS. 6A-6E illustrate a spectral library created by the inventors, with unique Raman spectra shown for each component of the eye. In these views, FIG. 6A shows the Raman spectrum associated with the lens, FIG. 6B shows the Raman spectrum associated with the retina, FIG. 6C shows the Raman spectrum associated with the cornea, FIG. 6D shows the Raman spectrum associated with the aqueous humor, and FIG. 6E shows the Raman spectrum associated with the vitreous humor. In some embodiments, the inventors hypothesized that the individual spectra in this spectral library may be added to an in vivo Raman spectra, such as that shown in FIG. 7A, to explain all of the shown frequencies. FIG. 7B illustrates a Raman spectra after regression analysis using the spectral library of FIGS. 6A-6E. In some embodiments, the regression analysis may be performed with a computer, with the algorithm arranged to try to explain each peak in the spectra using the spectral library. In some embodiments, once the peaks have been identified, the peaks may be interpreted. For example, in some embodiments, a higher peak may indicate a greater presence of a particular molecule in the retina.

As shown in FIG. 7B, the blue dot-dash line shows the raw Raman spectrum generated from a single excitation laser wavelength (optimized for each protein, reduced and oxidized). The orange solid line illustrates the frequencies (e.g., the fit) that can be explained from the Raman spectra shown in FIGS. 6A-6E. The grey line is a subtraction of the blue and orange lines, and represents the unknown unexplained residual after applying the spectra library to the regression analysis. As shown in FIG. 7B, after applying the spectral library from each eye and the molecule of interest, the spectra is almost completely explained, with little remaining residual. Thus, in some embodiments, the blue dot-dash line, showing the result of inelastic scattered light from different molecules in the tissue activated by a single laser wavelength, can be interpreted, and molecules can be distinguished from other molecules via the peak patterns (see the spectral library in FIGS. 6A-6E). In such embodiments, by knowing the peak pattern of the molecules in a tissue (e.g., via the spectral library), molecules in a tissue may be distinguished from other molecules in the tissue.

Figure 8A:
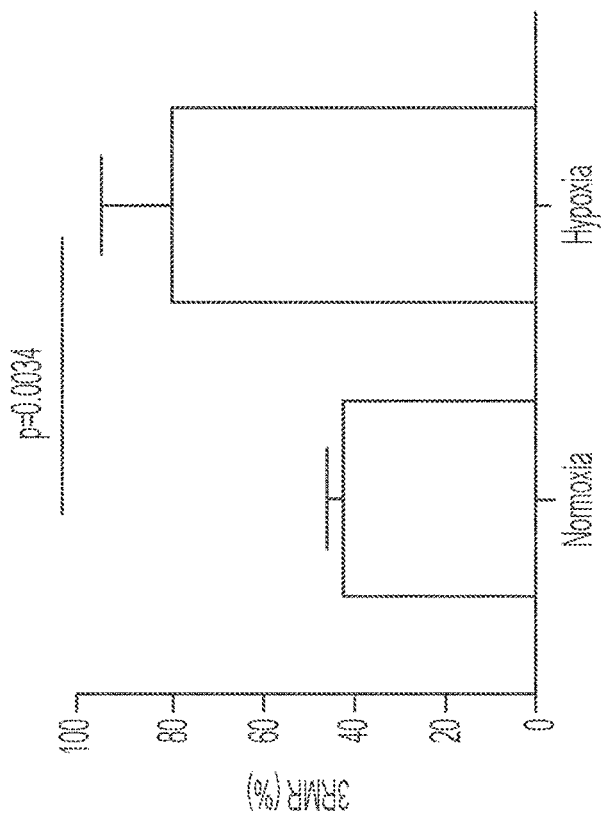
FIG. 8A illustrates reduced mitochondrial ratio (3RMR) changes in an in vivo retina under normoxia and hypoxia.

FIG. 8A illustrates an experiment in which hypoxia (11% $O_2$) was induced and evaluated via RRS. In such an experiment, the in vivo retina is first placed under a condition of normoxia (21% $O_2$), then under hypoxia, and finally in recovery returning to normoxia. As will be appreciated, during this time course, the retina is scanned using resonance Raman spectroscopy (e.g., with incident light at 441 nm), and the Raman spectrum for the retina is determined by adding the spectral library from FIGS. 6A-6E to a raw Raman spectra, such as that shown in FIGS. 7A and 7B. The representative mitochondrial ratio (3RMR) is calculated using the Raman spectra of the retina, with a representative 3RMR time course of the retina in vivo being shown in FIG. 8A. In some embodiments, a decrease of the final electron acceptor $O_2$ leads to an increase of the reduced mitochondrial ratio reflected in 3RMR.

Figure 8B:
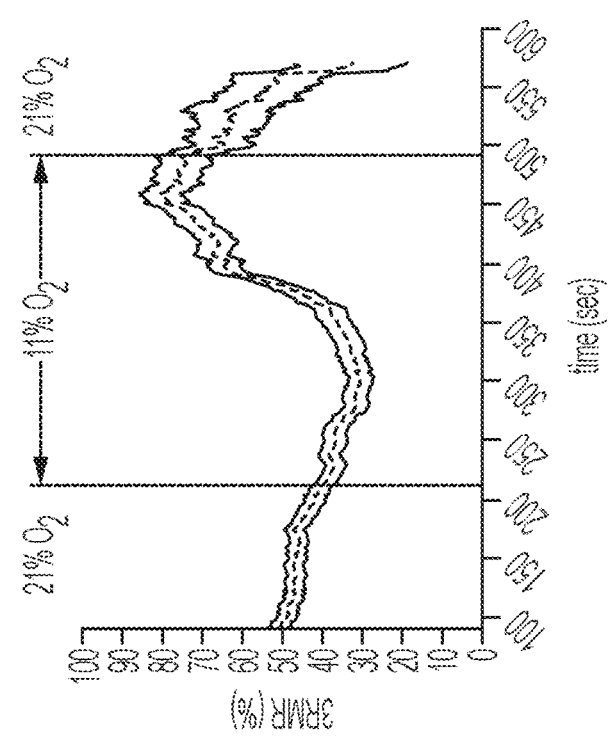
FIG. 8B illustrates peak 3RMR values of FIG. 8A under normoxia and hypoxia.

FIG. 8B shows peak 3RMR values under normoxia (21% $O_2$; n=4 eyes) and hypoxia (11% $O_2$; n=4 eyes). A two-way unpaired t-test was used for statistical analysis in this figure. The data represents the mean±standard deviation (SD).

Figure 12:
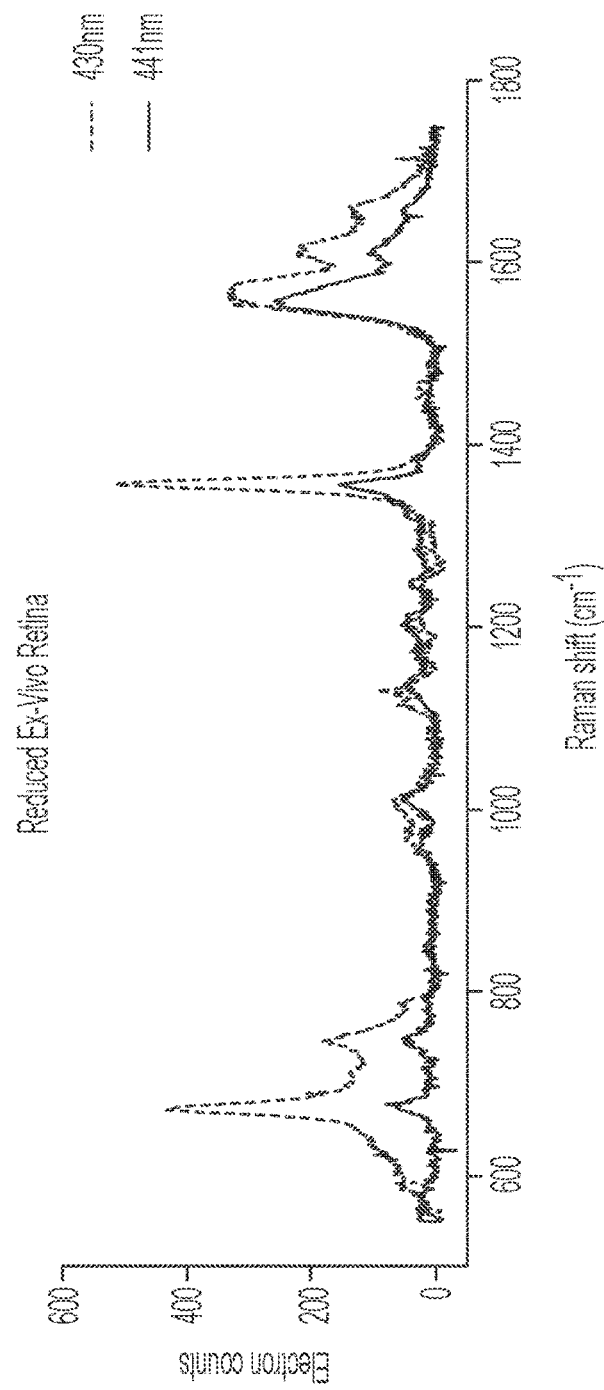
FIG. 12 is a Raman scattering of a reduced retina with 430 nm and 441 nm excitation.
Figure 13:
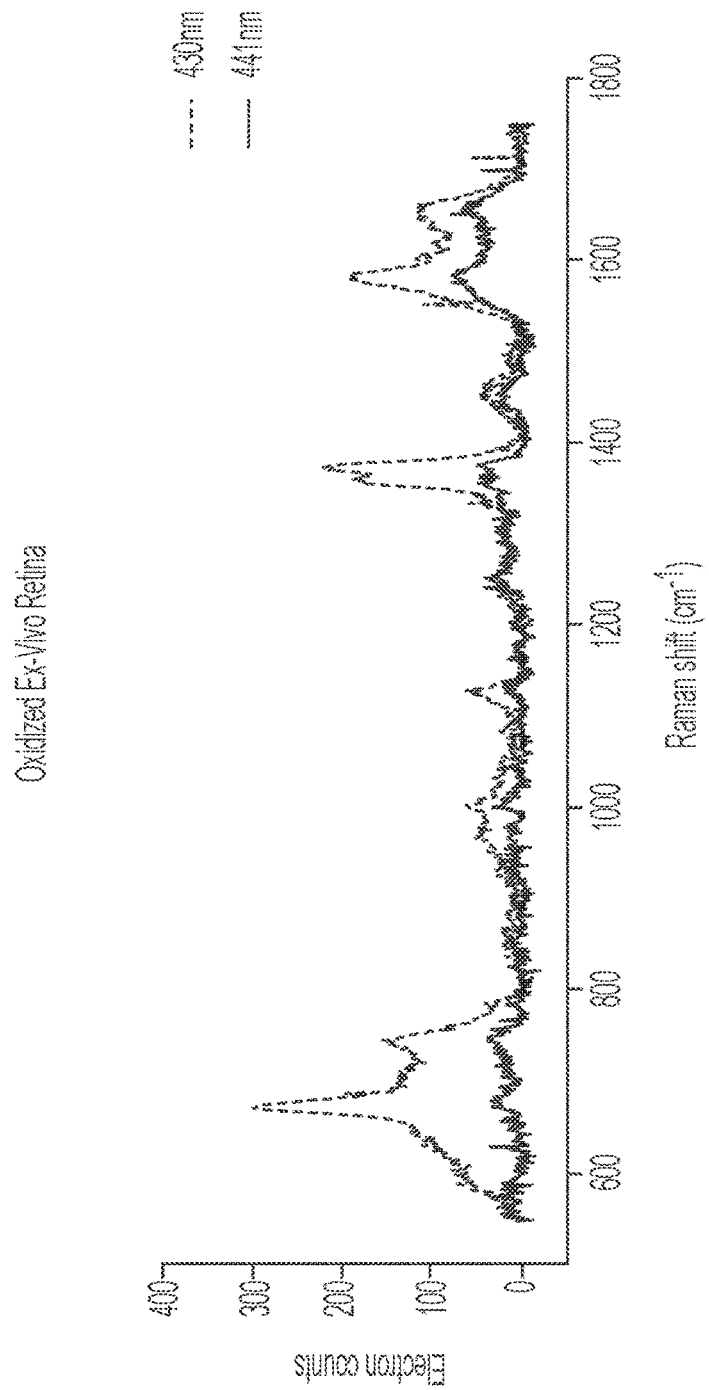
FIG. 13 is a Raman scattering of an oxidized retina with 430 nm and 441 nm excitation.

Although RRS of the eye has been described with an incident light having a wavelength of 441 nm, the retina may be excited with other incident lights, such as with a light having a wavelength of 430 nm. In some embodiments, as shown in FIGS. 12-13, which show Raman spectra for a reduced and oxidized ex-vivo retina, using a light with a wavelength of 430 nm may have more resonance, which may result in more defined peaks (e.g., higher intensity) on the Raman spectra (e.g., increased signal to noise ratio). Excitation with a wavelength of 430 nm also may result in a better balanced signature between the reduced and oxidized states. For example, as shown in FIGS. 12 and 13, at 441 nm, the peaks in the oxidized ex-vivo retina spectrum are not as pronounced (and possibly shifted) as compared to the peaks in the reduced ex-vivo retina spectrum. When the 430 nm light is used, peaks in both the reduced and oxidized ex-vivo retina spectrum are visible, with improved signal to noise ratio. In some embodiments, excitation via the 430 nm wavelength may allow for improved identification of the peaks using the spectral library (see, e.g., FIGS. 6A-6E) and less unexplained residual.

Figure 9B:
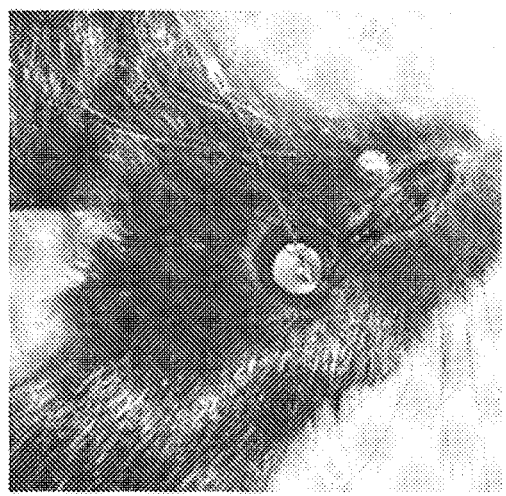
FIG. 9B is an image of a cannulated chamber of an eye of a mouse.
Figure 9A:
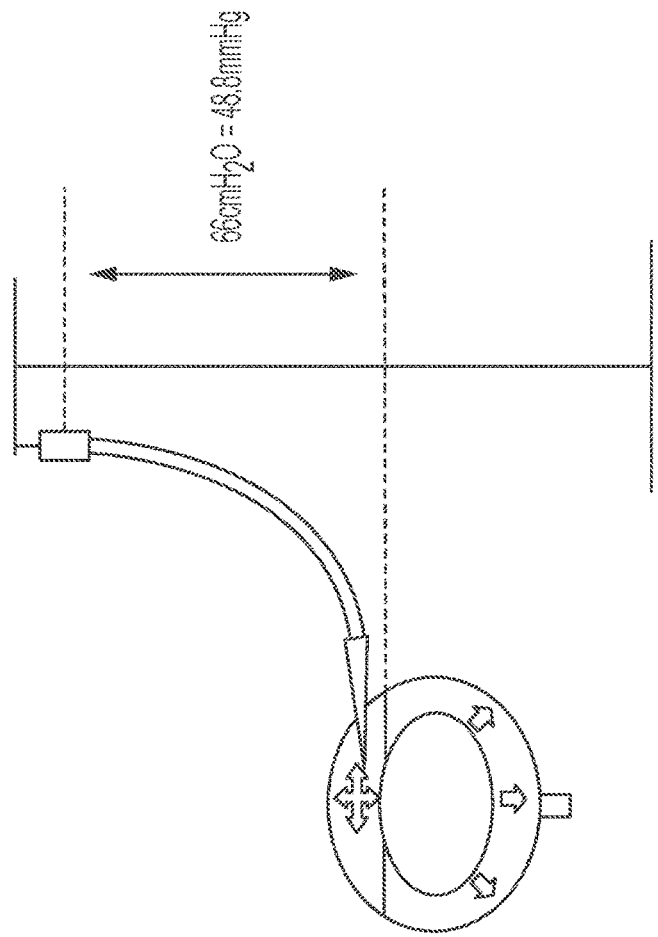
FIG. 9A illustrates a setup for simulating Glaucoma in a subject and testing a corresponding Raman spectra.
Figure 10:
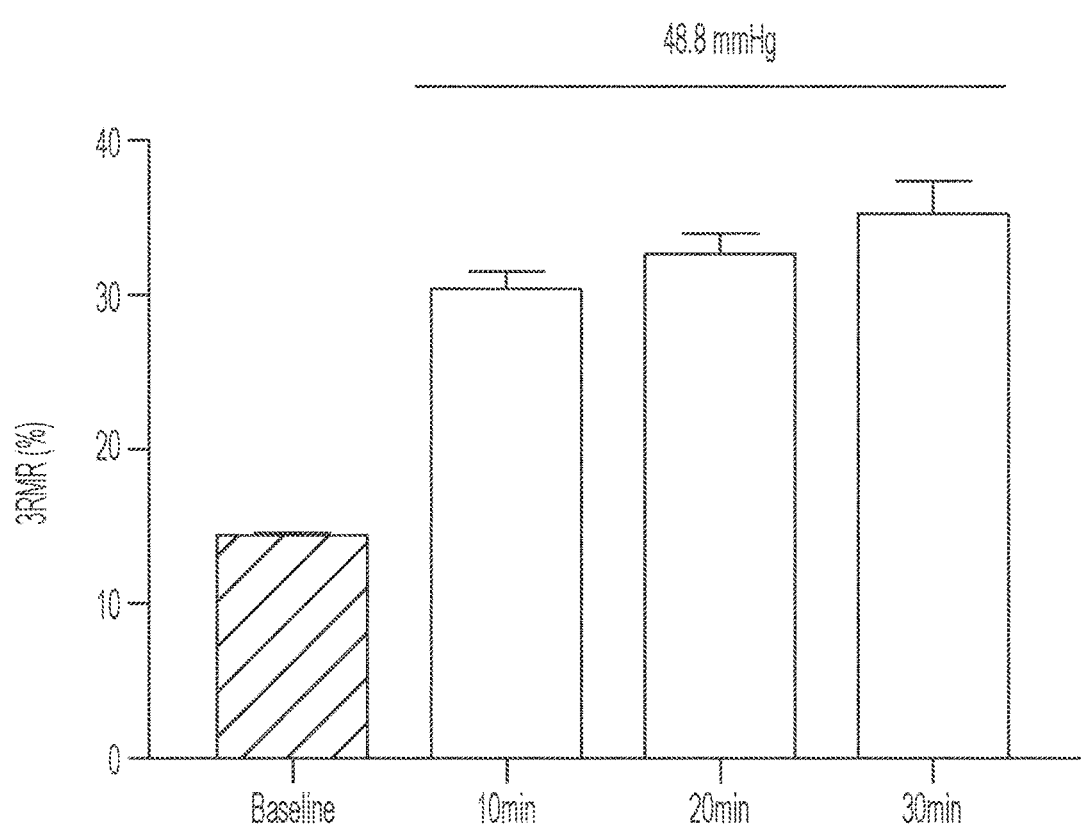
FIG. 10 illustrates a 3RMR of an optic nerve head at baseline, 10 minutes, 20 minutes, and 30 minutes after intra-ocular pressure (IOP) elevation to 48.8 mmHg.

FIG. 9A illustrates a setup of a glaucoma test in an eye. Without wishing to be bound by theory, glaucoma results when the pressure in the eye is too high, which may lead to cell death and permanent loss of vision. In some embodiments, the inventors hypothesized that a change in disease state may be mapped via the device. For example, as shown in FIG. 9A, using a cannulated anterior chamber connected to a fluid reservoir (e.g., by changing the height of the fluid reservoir), the inter-ocular pressure (IOP) of the eye of the mouse may be changed (e.g., increased). FIG. 9B shows an image of a cannulated anterior chamber of the mouse eye. In such embodiments, RRS testing was performed over a period of time (e.g., after 10 minutes, 20 minutes, 30 minutes), with the change in state being tracked. For example, in some embodiments, as shown in FIG. 10, RRS testing may show an increase in the reduced form over time. In some embodiments, the 3RMR values may be correlated with the particular disease state that was visualized. In some embodiments, the inventors have hypothesized that by correlating a particular disease state with a Raman reading, a later-measured Raman reading may be used to predict a possible disease state.

Figure 11:
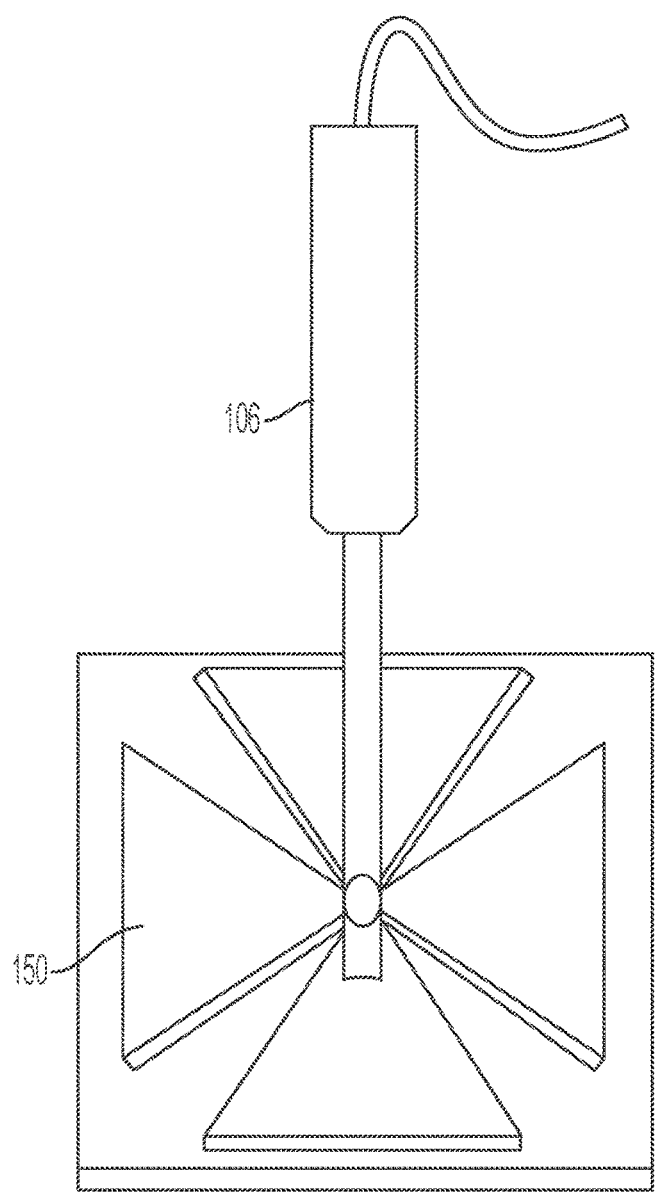
FIG. 11 is a schematic representation of an ex-vivo Resonance Raman measurement with an excitation wavelength of 440 nm and 430 nm.

FIG. 11 illustrates an example of a Raman probe passing an excitation laser source towards an ex-vivo retina 150. As will be appreciated, such a Raman probe may be a hand-held probe in some embodiments.

Although RRS has been described as being conducted with a system such as that shown in FIGS. 1 and 2, it will be appreciated that other suitable configurations may be used to conduct RRS on a subject. For example, a contact lens may be designed to be placed on a subject, the contact lens being capable of providing a light source and gathering Raman signals, which are thereafter communicated to a computer system that transforms the readings into a Raman spectra.

As will be appreciated, although the RRS apparatus is shown and described as performing RRS on a rodent, the RRS apparatus may be used to perform RRS on other subjects, such as human subjects. In one such example, the subject may be asked to rest his face in or against a portion of the system (e.g., putting his chin in a cradle and resting his forehead against a portion of the apparatus) to align the subject's eye with the probe having the light source.

Although the same device is shown and described as performing both RRS on and imaging of a subject, the device may be arranged to perform only RRS on the subject or to only image the subject. For example, the testing device 100 may be arranged to perform only RRS on the subject, while a second device is arranged to image the subject. As will be appreciated, in such embodiments, a RRS spectra from a first testing device that performs RRS on the subject may be correlated with an image from a second testing device that images the subject.

Additionally, although RRS has been shown and described for use in metabolic mapping of the retina, RRS mapping of the retina (or of another part of the eye) can be used for other ophthalmologic purposes. For example, Applicant has recognized that RRS may be used to create protocols for treating ophthalmologic diseases.

As is known, for certain ophthalmologic diseases, anti-vascular growth factors are injected into the eye. Unfortunately, the antibodies that are used to suppress vascularization in the eye also may have systemic side effects. Additionally, the same dose of antibodies is typically used for all patients, and all patients do not have the same need for such antibodies. Accordingly, RRS may be used to determine the level of a particular antibody in the eye, with a dose of the antibody calculated based on the difference between the target level of the antibody an the actual level of the antibody present in the eye. This calculated dose may then be injected into the eye, which may avoid overtreatment and potential side effects. In addition, this may lead to less anti-VEGF injections into the eye, which may result in decreased health care costs and an increased quality of life for the patient.

In one embodiment, such as when the retina becomes hypoxic, the retina begins to express VEGF. In such an embodiment, RRS of the retina may be used to determine the level of VEGF present, and the dose of VEGF given to the subject to treat a particular disease may be determined based on the difference between the actual level of VEGF in the eye and the target level of VEGF.

Figure 14:
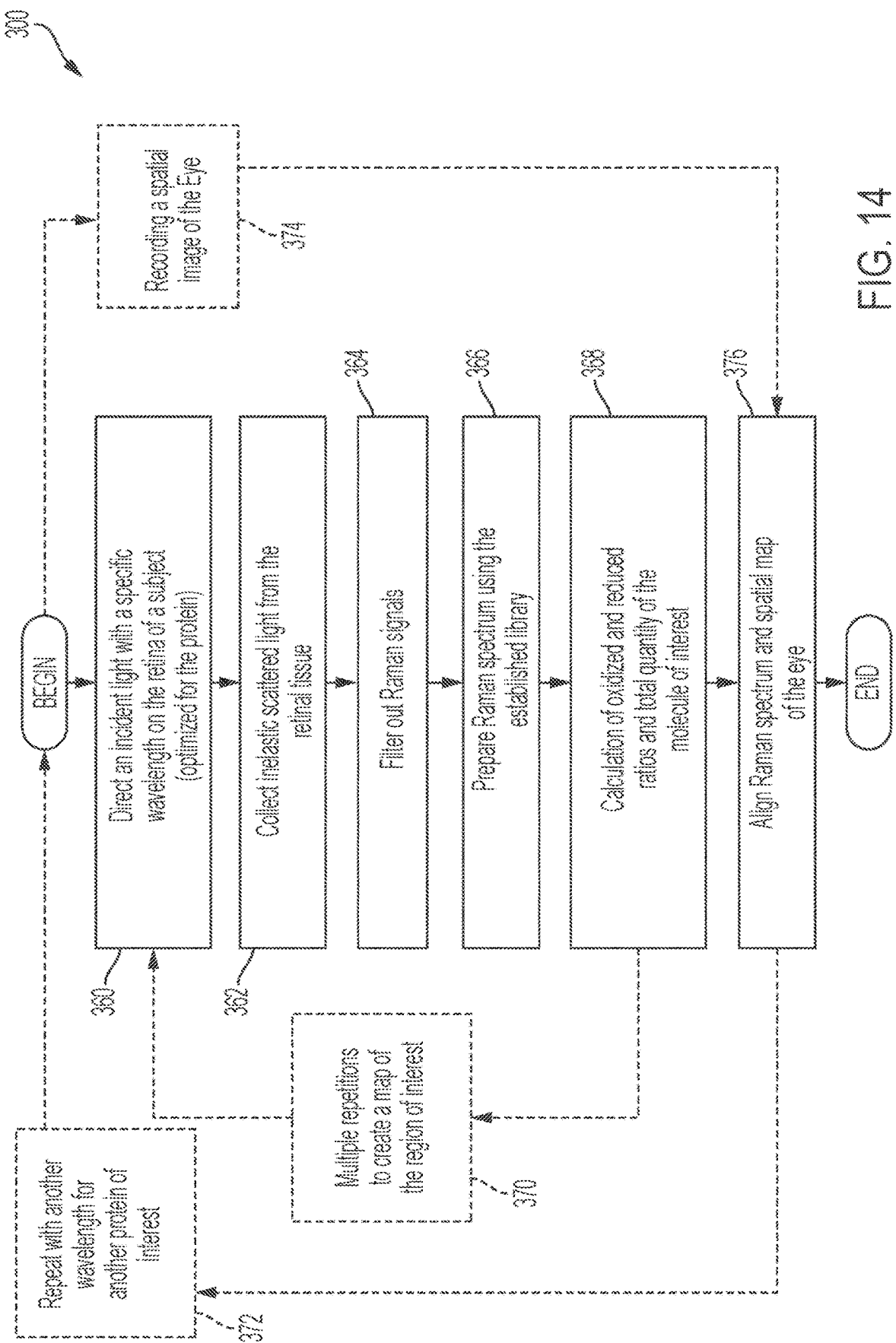
FIG. 14 illustrates a method of metabolically mapping a retina according to some embodiments.

FIG. 14 illustrates a method of metabolically mapping the retina 300. As shown in this figure, the method includes directing a light source onto a retina of a subject via RRS 360. Next, the inelastic scattered light from the retinal tissue may be collected 362. The Raman signals may then be filtered out from the inelastic scatter 364. Next, using the established spectral library (see, e.g., FIGS. 6A-6E), a Raman spectrum for the retinal tissue may be prepared 366. Using this spectrum, the oxidized and reduced ratios and total quantity of the molecule of interest (e.g., oxygen) may be calculated 368. In some embodiments, these steps may be repeated one or more times to create a map of the region of interest 370. For example, a 441 nm incident light or a 430 nm incident light may be directed over the retina one or more times, with a resulting calculation of the oxidized and reduced ratios and total quantity of the molecule of interest being performed.

In other embodiments, the steps may be repeated using a different wavelength of incident light to detect another protein of interest 372. For example, after performing these steps using a 441 nm incident light, the eye may then be scanned with a 400 nm incident light. As with the previous embodiments, after the light is detected, the inelastic scatter can be collected, the Raman signals can be filtered, a Raman spectrum may be prepped, and a calculation of the oxidized and reduced ratios and the total quantity of the molecule of interest may be performed. As will be appreciated in view of the above, the wavelength may optimized based upon the molecule being detected to improve the signal to noise ration.

In some embodiments, as also shown in FIG. 14, metabolically mapping the retina also may include recording a spatial image of the eye 374. For example, OCT or fundus photography may be used to create a spatial image of the eye. In some embodiments, the spatial mapping is performed before, during or after the scattered light is collected. The spatial mapping also may be performed at other suitable times. In some embodiments, the Raman spectrum is aligned with the spatial map of the eye 376 to allow a histological change to be associated with the particular Raman spectrum (and also the determined oxygenation level).

Figure 15:
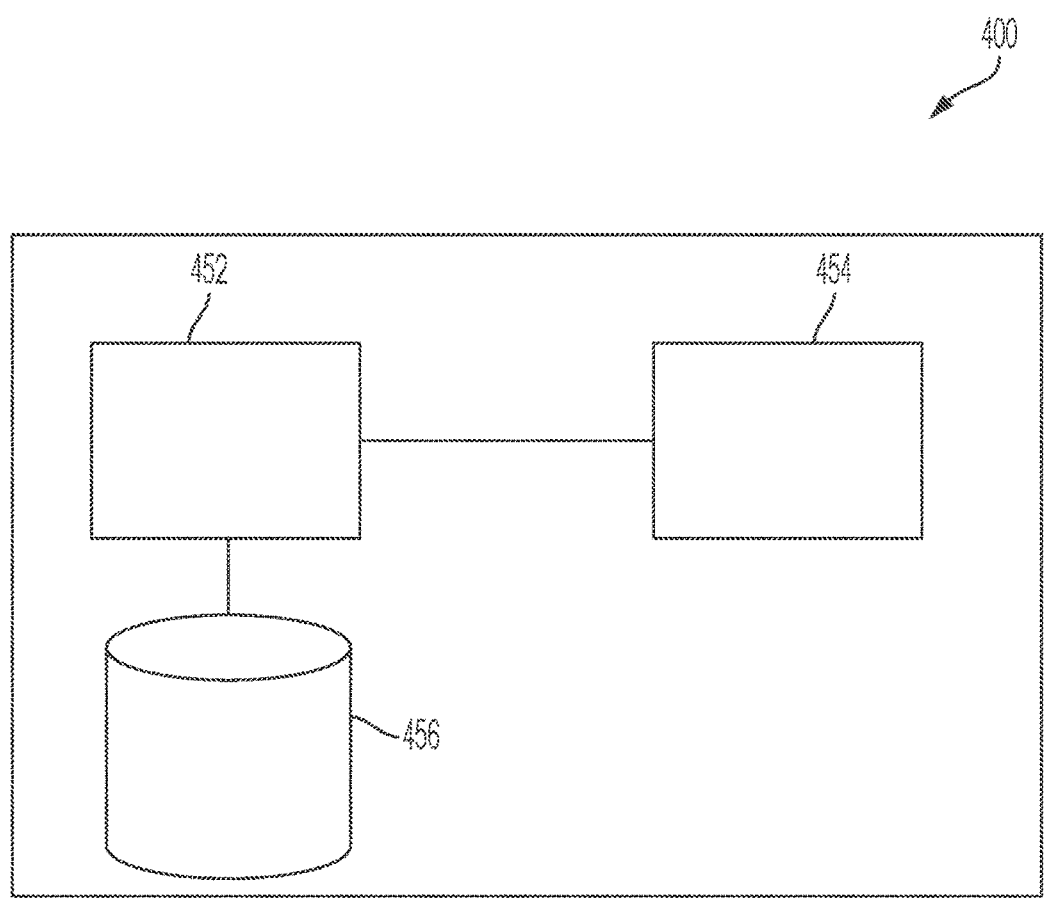
FIG. 15 is a schematic view of a computer system according to one embodiment.

An illustrative implementation of a computer system 400 that may be used in connection with some embodiments of the present invention is shown in FIG. 15. One or more computer systems such as computer system 400 may be used to implement any of the functionality described above. The computer system 450 may include one or more processors 452 (e.g., processing circuits) and one or more computer-readable storage media (i.e., tangible, non-transitory computer-readable media), e.g., volatile storage 454 (e.g., memory) and one or more non-volatile storage media 456, which may be formed of any suitable non-volatile data storage media. The processor(s) 452 may control writing data to and reading data from the volatile storage 454 and/or the non-volatile storage device 456 in any suitable manner, as aspects of the present invention are not limited in this respect. To perform any of the functionality described herein, processor(s) 452 may execute one or more instructions stored in one or more computer-readable storage media (e.g., volatile storage 454), which may serve as tangible, non-transitory computer-readable media storing instructions for execution by the processor 452.

The above-described embodiments of the present invention can be implemented in any of numerous ways. For example, the embodiments may be implemented using hardware, software or a combination thereof. When implemented in software, the software code (e.g., instructions) can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present invention comprises at least one computer-readable storage medium (i.e., at least one tangible, non-transitory computer-readable medium, e.g., a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present invention.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:
1. A device comprising:
a Raman spectrometer arranged to collect inelastic light;
a Raman probe in communication with the Raman spectrometer, the Raman probe arranged to transmit light to a portion of a subject and collect the inelastic light back to the spectrometer; and a first imager arranged to capture a spatial image of the portion of the subject,
wherein the device is configured to generate a Raman spectrum from the collected inelastic light, and wherein the device is configured to calculate an oxidized ratio, a reduced ratio, and a total quantity of a first molecule using the Raman spectrum.

2. The device of claim 1, further comprising one or more processors configured to generate the Raman spectrum from the collected inelastic light, and wherein the one or more processors are configured to align the Raman spectrum with the spatial image of the portion of the subject.

3. The device of claim 1, further comprising an objective lens, the objective lens being in communication with each of the Raman probe and the first imager.

4. The device of claim 1, further comprising a scanning mirror arranged to adjust a scanning area of the Raman probe.

5. The device of claim 1, further comprising an excitation source arranged to supply an excitation laser to the Raman probe.

6. The device claim 1, further comprising one or more beam splitters.

7. The device of claim 1, wherein the first imager includes one of a fundus camera and an anterior segment camera.

8. The device of claim 1, wherein the Raman spectrometer includes a filter and a charge coupled device detector.

9. The device of claim 1, further comprising one or more processors configured to generate the Raman spectrum from the collected inelastic light, and wherein the one or more processors are configured to calculate the oxidized ratio, the reduced ratio, and the total quantity of the first molecule using the Raman spectrum.

10. The device of claim 1, wherein the light transmitted by the Raman probe has a wavelength of one of 441 nm and 430 nm.

11. The device of claim 1, wherein the device is configured to align the Raman spectrum with the spatial image of the portion of the subject to associate a histological change of the subject with the Raman spectrum.

\* \* \* \* \*